United States Patent [19]
Berndt et al.

[11] Patent Number: 5,383,862
[45] Date of Patent: Jan. 24, 1995

[54] METHOD AND DEVICE FOR ENVELOPING AND DISINFECTING OF SHARP INSTRUMENTS

[76] Inventors: Dieter R. Berndt, 3407 Sandpiper Way, Allenwood, N.J. 08720; Brian P. Smith, 409 St. Clair Ave., Spring Lake, N.J. 07762

[21] Appl. No.: 167,538

[22] Filed: Dec. 14, 1993

Related U.S. Application Data

[63] Continuation-in-part of Ser. No. 4,181, Jan. 13, 1993, abandoned, which is a continuation of Ser. No. 829,894, Feb. 3, 1990, abandoned.

[51] Int. Cl.⁶ .................................. A61M 5/00
[52] U.S. Cl. .................................. 604/187; 604/263; 206/365
[58] Field of Search ............... 604/187, 192, 110, 162, 604/163, 263; 206/364, 365

[56] References Cited
U.S. PATENT DOCUMENTS

| | | |
|---|---|---|
| 2,969,330 | 1/1961 | Brynko. |
| 3,137,631 | 6/1964 | Soloway. |
| 3,341,466 | 9/1967 | Brynko et al. . |
| 3,516,943 | 6/1970 | Brynko et al. . |
| 4,026,287 | 5/1977 | Haller. |
| 4,254,179 | 3/1981 | Carson, III et al. . |
| 4,596,562 | 6/1986 | Vernon . |
| 4,758,229 | 7/1988 | Doerschner . |
| 4,875,896 | 10/1989 | Kurtz .................. 604/187 |

Primary Examiner—John D. Yasko
Attorney, Agent, or Firm—Harness, Dickey & Pierce

[57] ABSTRACT

A device for enveloping and disinfecting of sharp instruments includes a main body portion having an upper surface and a lower surface. Attached to the lower surface is a protective layer. Provided on the upper surface is an adhesive at least immediately adjacent the perimeter thereof and an anti-virus and anti-bacterial disinfectant material. The disinfectant is incorporated into composite dispensing member including a plurality of microcapsules, each of said microcapsules including an active disinfecting ingredient. The plurality of microcapsules are sufficiently frangible so as to rupture upon application of a predetermined stress.

19 Claims, 2 Drawing Sheets

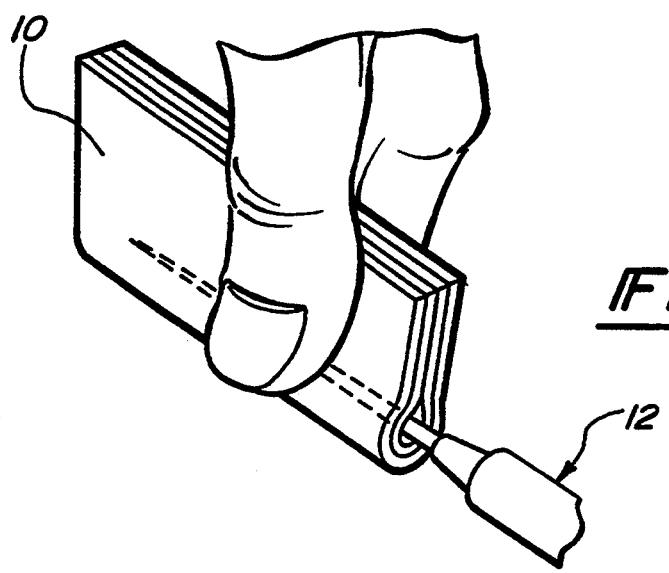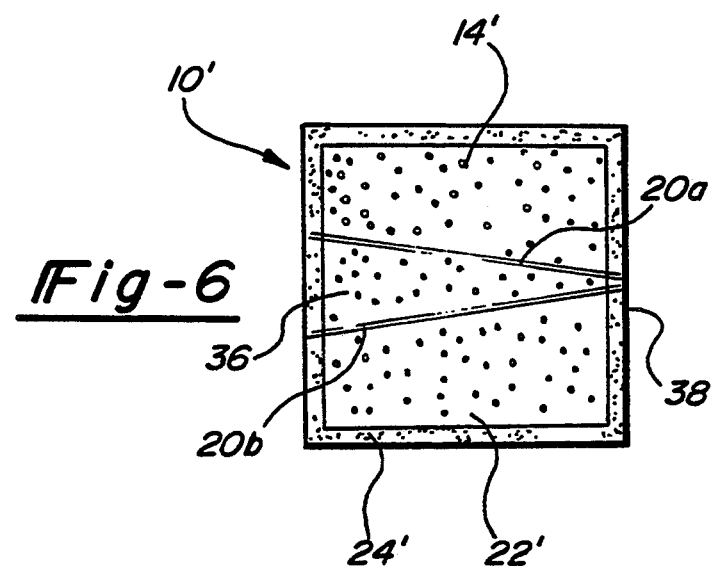

METHOD AND DEVICE FOR ENVELOPING AND DISINFECTING OF SHARP INSTRUMENTS

This application is a continuation-in-part application of Ser. No. 08/004,181, filed Jan. 13, 1993 now abandoned, which is a continuation of application Ser. No. 07/829,894, filed Feb. 3, 1992, now abandoned.

BACKGROUND OF THE INVENTION

The present invention in general relates to the disposal and decontamination of potentially contaminated sharp instruments. More specifically, the present invention relates to a method and device for discarding and decontaminating potentially contaminated sharp instruments by enveloping the sharp instrument between a folded pad having an adhesive surface and microencapsulated disinfectant.

A large percentage of hospital-related injuries are attributable to accidental sticks from sharp instruments including needles, scalpels and the like. A high incidence of such injuries also inflicts laboratory personnel and nursing and physician personnel. Furthermore, housekeeping personnel often suffer from such injuries. Typically, injuries resultant from accidental needle and scalpel sticks occur after the instruments have been used. As a result, affected personnel are subject to serious diseases, including but not limited to AIDS and Hepatitis B.

Most often, needle and scalpel sticks occur during the handling of sharp instrumentation prior to permanent disposal. The carrying of such instruments to designated containers, placing them in the containers and emptying the containers have proven to be a common source of injury. Often needles dangerously protrude from waster containers. Additionally, attempting to re-cap disposable syringes often results in inadvertent needle sticks. In this regard, if the needle misses the opening in the cap during recapping, the hand of the personnel holding the cap is often accidentally stuck and thereby exposed to any fluid-borne infection carried by the needle. To avoid this specific problem, the Center for Disease Control currently recommends discarding disposable syringes without replacing the cap. This essentially requires personnel to deliver a disposable syringe, exposed and potentially contaminated, to an approved medical waste disposition container. The probability of an accidental needle stick becomes even greater since additional personnel are necessarily involved during transit to the medical waste disposition container and also upon periodic emptying of the container.

Injuries produced from accidental sticking by contaminated sharp instruments have been documented as the cause of severe illness and have even resulted in death. Additionally, such injuries result in unnecessary pain and often extensive testing to determine the extent of injury or infection or both. Furthermore, injured personnel often suffer from the anxiety affects of stress due to the potential risk involved with the accidental transfer of bodily fluids.

To address the problems associated with the proper disposal of sharp instruments, many prior art techniques and devices have been employed. One such technique, commonly referred to as "scooping", involves lifting the cap of the disposable needle off a table top with the needle and pressing the cap against a hard surface to seat the cap on the needle hub or base. One such device employed to alleviate accidental needle stick injuries is a single use syringe which is disposable. An example of this approach is illustrated in U.S. Pat. No. 4,026,287 issued to Haller. Another such device is adapted to hold a needle cap so that the needle can be reinserted into the cap while keeping hands out of the area of potential danger. U.S. Pat. No. 4,596,562 to Vernon is an example of such a hand held device of this type.

While prior art techniques and devices have successfully lowered the incidents of accidental needle sticks, each known technique or device involves inherent limitations. Some of the techniques and devices are only suitable for disposable syringes. Other of the techniques and devices are awkward at best and cannot easily be employed in a surgical or emergency setting. Still yet other of the techniques and devices do not comply with the recommendation of the Center for Disease Control to discard disposable syringes without replacing the needle cap. Further, none of the known techniques and devices properly decontaminate potentially infected sharp instruments. Additionally, many prior techniques and devices are complex and cost prohibitive.

Accordingly, it is desired to provide an apparatus for enveloping and decontaminating sharp instruments of the type used in contact with potentially infected bodily fluids prior to disposal of the sharp instruments.

SUMMARY OF THE INVENTION

Generally, the present invention provides an apparatus for enveloping and decontaminating a sharp instrument prior to disposal thereof, the sharp instrument being of the type used in contact with potentially infected bodily fluids, in which the apparatus includes a disinfectant for eliminating infectious diseases. The invention also encompasses a method for enveloping and decontaminating a sharp instrument prior to disposal thereof.

More specifically, in one aspect of the invention, the apparatus for enveloping and decontaminating a sharp instrument includes a substantially planar main body member having first and second sides. The first side includes a first portion and a second portion. The main body member is sufficiently flexible to permit the first portion to be folded over onto the second portion. The apparatus further includes a flexible sheet material permanently attached to the first side, the sheet material being resistant to penetration by the sharp instrument. A first area of adhesive is formed on the first portion and a second area of adhesive is formed on the second portion. Preferably, a microencapsulated disinfectant is provided on at least one of the first and second portions of the main body member.

In another aspect of the invention, a method for enveloping and decontaminating a sharp instrument prior to disposal thereof consists of the step of providing an apparatus including a substantially planar main body member having first and second sides, the first side including a first portion and a second portion. Both of the first and second portions include a first end and a second end. The main body member is sufficiently flexible to permit the first portion of the main body member to be folded over onto the second portion of the main body member. The apparatus further includes a flexible sheet material permanently attached to the first side which is resistant to penetration by sharp instruments. The method further includes the step of applying adhesive to the first portion and the second portion of the main body member and folding over the first end of the first portion until it contacts the first end of the second portion. Next, the method of the present invention includes the step of forming the main body portion into a cradle-like shape for receiving the sharp instrument by applying pressure to the second side adjacent the first ends of the first and second portions to thereby adhere the first portions together. Next, the method of the present invention includes the steps of placing a sharp instrument on the first side of the main body portion and folding the second end of the first portion until it contacts the second end of the second portion.

A primary object of the present invention is to substantially eliminate accidental sticks from sharp instruments such as needles, scalpels and the like by providing an apparatus for enveloping and decontaminating the sharp instrument.

An advantage of the present invention is to provide an apparatus for enveloping a potentially contaminated sharp instrument which is adapted to disinfect the sharp instrument of fluid-borne infection.

Another advantage of the present invention is to provide an apparatus for enveloping and decontaminating a potentially infected sharp instrument which can be prepared prior to use so that the process of enveloping and decontaminating the sharp instrument can be accomplished with only one hand.

A further advantage of the present invention is to provide an apparatus for safely disposing a sharp instruments which complies with the Center for Disease Control recommendation of discarding disposable syringes without replacing the needle cap.

It is therefore another object of the present invention to provide a new dispensing material for storing, applying, releasing, and dispensing active ingredients from micropackaged particles such as microcapsules and polymer lattices.

Yet another object of the invention is to provide a composite dispensing material with intimate bonding between micropackaged active ingredient particles and a foam substrate, so that particles are not lost.

A further object of the invention is to provide a new method for producing a composite material of open foam substrate and micropackaged active ingredient particles in which particles are not ruptured or active ingredient lost during intimate bonding between the particles and substrate.

Yet another advantage of the present invention is to provide an apparatus for enveloping and decontaminating a sharp instrument which is inexpensive.

Still yet another object of the present invention is to provide an apparatus for substantially bringing a potentially infected sharp instrument within medical waste control immediately after use.

BRIEF DESCRIPTION OF THE DRAWINGS

The various objects and advantages of the present invention will become apparent to those skilled in the art after reading the following specification and by reference to the drawings in which:

FIG. 5 is a perspective view of the apparatus of FIG. 1 shown enveloping a needle of a disposable syringe; and FIG. 6 is a top view of a second preferred embodiment of the present invention illustrated with diverging predetermined fold lines.

DETAILED DESCRIPTION OF THE PREFERRED EMBODIMENTS

Referring now to FIGS. 1–5, there is shown an apparatus 10 for enveloping and decontaminating a potentially infected sharp instrument constructed in accordance with the first embodiment of the present invention. It will be understood that while the apparatus 10 of the present invention is illustrated for use with a disposable surgical syringe 12, the teachings of the present invention are not limited thereto and the drawings merely illustrate an exemplary use. In this regard, it will be appreciated by those skilled in the art that the teachings of the present invention are readily adapted for envelopment and decontamination of other sharp instruments, including but not limited to detachable needles, sutures, scalpels and the like.

The preferred embodiment of the apparatus 10 of the present invention includes a substantially planar main body member 14 having first and second sides. In the exemplary embodiment illustrated, the apparatus 10 is rectangular in configuration and is approximately 2"×3". However, it should be appreciated by those skilled in the art that the present invention is not limited to a particular size. In this regard, the size of the apparatus 10 is dictated by the size of the sharp instrument to be enveloped therein. For example, particular circumstances, such as those involving a known infection or for needle uses remote from a proper waste container, it may be desirable that the main body member 14 be sufficiently large to fully envelope an entire disposable syringe 12.

Preferably, the main body member 14 is constructed of a fabric, such as a non-woven fabric, that, preferably, has been treated to resist or retard fluid transmission. Alternatively, the main body member 14 may be formed of a compressed foam material such as a one-pound density closed cellular polyethylene foam.

Figure 1:
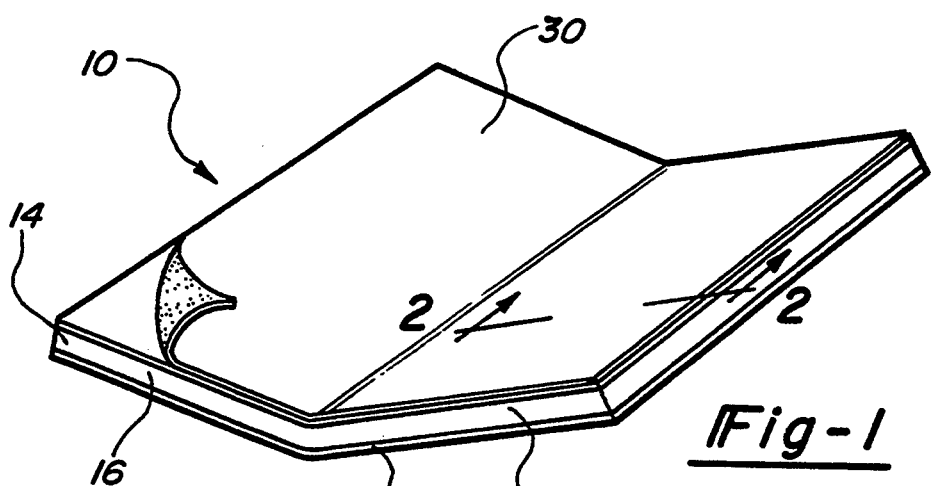
FIG. 1 is a perspective view of an apparatus for enveloping and decontaminating a sharp instrument according to the first preferred embodiment of the present invention.
Figure 2:
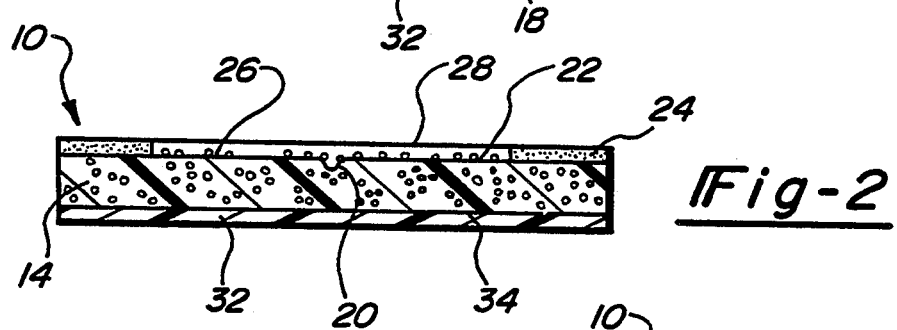
FIG. 2 is a cross-sectional view of the apparatus for enveloping and decontaminating a sharp instrument of FIG. 1 taken through the lines 2—2 thereof.

As shown in FIG. 1, the main body member 14 includes first and second portions 16,18 which are substantial mirror images of one another about a midline of the main body member 14. In the preferred embodiment, coincidental with the midline of the main body member 14 is a predetermined fold-line 20.

The first surface, or upper surface 22, of the main body member 14 is covered with a layer or coating of pressure-sensitive adhesive 24. Acrylate-base adhesives have been found effective, but any suitable pressure-sensitive adhesive having a high degree of surface tack may be used. Alternatively, the adhesive 24 may be limited to areas of the main body member adjacent the periphery.

The first embodiment of the present invention further includes a disinfectant material disposed on the upper surface of the main body member 14 over the adhesive. Sodium hypochlorite has been found to be effective, but any suitable disinfectant such as anti-viral and anti-bacterial agents, including but not limited to those recommended by the Center for Disease Control, may be used. Preferably, the disinfectant material is not applied to the area of the main body member immediately adjacent the periphery thereof. As such, the adhesive 24 necessary to substantially permanently enclose the main body portion 14 upon folding is not subject to degradation. Alternatively, strips of adhesive may be interleaved between strips of disinfectant material. The strips may be disposed either diagonally or normal to the edges of the main body member 14.

Further preferably, the disinfectant material is provided on the main body portion 14 in micro-encapsulated form. The microcapsules 26 are preferably manufactured by microencapsulation, a process well known in the art. In general, in microencapsulation small droplets of a functional ingredient, whether an active liquid or solid, are coated with a continuous film of polymeric material. Microencapsulation is accomplished by a conservation process. More specifically, a microcapsule wall-forming liquid polymer or coating, commonly referred to as the coacervate, is deposited on droplets or particles of the functional ingredient which are in turn dispersed in a liquid vehicle or carrier. The wall coating forms during controlled physical mixing of the liquid vehicle, functional ingredient, and coating material or coacervate. The liquid coating material is solidified, thereby encapsulating the functional ingredient, while the temperature of the liquid carrier is lowered at a specific Ph. The process of microencapsulation and formation of microcapsule systems is further described in the *Encyclopedia of Chemical Technology*, Vol 13, J. A. Herbig, "Microencapsulation", pp. 436–456, John Wiley & Sons, Inc., 2nd edition, 1967, and various United States patents including U.S. Pat. Nos. 2,969,330, 3,137,631, 3,341,466, 3,516,943 and 3,415,758, all of which are hereby incorporated by reference as if fully reproduced herein.

It will he appreciated by those skilled in the art that the microcapsules 26 can alternatively be formed by entrapment, also a process well known in the art. Briefly, in entrapment the active liquid, ingredient, or functional material is contained by sorption within a microscopic matrix or lattice. The lattice containment results in conversion, for example, of liquids, waxes or solids into free-flowing particles.

Polymer entrapment systems are available from Wickhern Products, Inc., Big Pond Road, Huguenox, N.Y. 12746, under the trademark POLYTRAP ™. Typical polymer entrapment particles range in particle size from less than 45 microns to, for example, 3,000 microns, that is from powders to beads. The characteristics of the entrapment materials may he varied according to the lattice wall copolymers and the ratio or percentage of copolymers comprising the particles.

Such micropackaging and microcontainment systems are applicable for storage and protection of active ingredients both liquid and solid, particularly where volatilization otherwise reduces the life or changes the characteristics of the functional material. Micropackaging by encapsulation or entrapment serves to protect the active liquids or solids from deterioration and exposure to air or even lights, and increases longevity. For example, micropackaging is known to enhance and improve the fidelity and longevity of emollients, fragrances, and oils. The micropackaging can be designed to provide slow release of a controlled ingredient, long-lasting continuous release by diffusion, or other sustained release patterns.

The microcontainment walls of the microcapsules 26 may be formed to include one or more layers selected from a variety of coacervates including, but not limited to gelatin, waxes, polyethylene, polypropylene, urea-formaldehyde, polyamides, ethocel and polymeric food grade substances. The particular coacervate or combination of coacervate can be selected to provide protection against a number of environmental effects including, but not limited to sunlight, photosensitization, microbiological contamination, chemical changes, and exposure to the microenvironment. The wall construction of the microcapsules can also be adapted to respond to any of a number of defined environmental stresses for breaking or rupturing the microcontainment walls and releasing the active solid or liquid ingredient contained by the micropackaging. Thus, the microcapsules 26 may be designed, constructed, and arranged to provide the controlled or continuous release of the variety of active ingredients contemplated by the present invention. Through the incorporation of microcapsules, the present invention provides an ability to utilize a wider range of disinfectant due to extended shelf life. As a result, stronger, often more effective, disinfectants can be used. Further, manufacturing costs are often reduced.

In the exemplary use illustrated throughout the Figures, the microcapsules 26 are formed with fragile mircrocontainment walls for breaking and releasing the active ingredient in response to predefined pressure, such as that which results through gentle manual squeezing. It will be appreciated by those skilled in the art, that particular applications may require the container walls to rupture or otherwise break in response to a desired level of rubbing or abrading, heating, light exposure, biodegradation, dissolving of the wall, diffusion, Ph change or other stress. This responsive rupture can be conditioned through the wall thickness and material.

The microcapsules 26 of the present invention may range from powder size, for example in the range of 1 to 4 microns, to granular and bead sizes from 2,000 to 5,000 microns. A preferred size range of 400 to 1,000 microns is used in a variety of applications. The particle size ranges of 400 to 1,000 microns affords the advantage of apparently invisible or small size while imparting the sensible or tactile feel of breaking and releasing in response to pressure or abrasion.

Preferably, the microcapsules 26 of the present invention are incorporated into a layer of composite dispensing material 28. The composite dispensing material 28 includes an open foam substrate and the microcapsulated active ingredient particles. The foam substrate is generated by foam polymerization of a prepolymer phase and an aqueous phase. The foam substrate is an open cell foam for dispensing the active ingredient liquids or solids released from the microencapsulated particles.

The aqueous phase is a pourable and flowable slurry mixture of an aqueous liquid carrier such as water, microencapsulated active ingredient particles generally in the range of 1%–60% by weight of the aqueous phase, and a surfactant wetting agent for adjusting the surface tension of the aqueous phase to produce an open cell foam upon polymerization with the prepolymer phase. The prepolymer phase is preferably a hydrophilic polyurethane prepolymer receptive to the aqueous phase for foam polymerization upon mixing. The aqueous phase and prepolymer phase are generally mixed together in a ratio by weight of aqueous phase to prepolymer phase in a range of at least approximately 0.2/1 or greater and preferably 1/1 or greater.

Upon foam polymerization, the microcapsules 26 containing the active ingredient particles are distributed over and intimately bonded to the surfaces of the open foam substrates. According to a preferred example, the aqueous phase is formulated so that the open foam substrate is a reticulated foam with the microcapsulated active ingredient particles distributed over and bonded to the webs of the reticulated foam. Furthermore, the micropackaged active ingredient particles are distributed and intimately bonded throughout the foam substrate thereby protecting the microcapsules 26 from the disadvantages of mechanical handling and abrasion and the resultant premature release of the active ingredient typically associated with microencapsulation systems.

The resulting composite material of foam substrate and intimately bonded microcapsules 26 is formed with the microcapsules 26 preferably composing in the range of 1%–80% by weight of the composite material. The range of percentage composition of microcapsules 26 active ingredient particles determines the rate and volume of "expression" of active ingredient upon application of pressure, abrasion or other environmental eliciting parameter to the composite dispensing material 28. At the lower density end of the range, for example, several percent by weight of microcapsules 26, the composite foam substrate expresses only a trace of fluid or other active ingredient upon compression, abrasion or other selected stress. At the higher end of the range approaching 80%, a visible flow of liquid or other active ingredient is expressed by the composite dispensing material 28.

Alternatively, the composite dispensing material 28 incorporates a fabric skeleton or matrix (not shown) impregnated with the foam substrate, thereby interpenetrating the foam substrate. The fabric skeleton or matrix is preferably a nonwoven material which may be of desired contour. The open foam substrate bonds to fibers and fills the interstices of the nonwoven fabric skeleton or matrix, while the micropackaged active liquid or active ingredient particles are distributed over and intimately bonded to the surfaces of the open foam substrate as described above.

The composite dispensing material 28 of the present invention is attached directly to at least a portion of the upper surface 22 of the main body portion 14. The composite dispensing material 28 is firmly held in place by the adhesive 24 provided on the upper surface 22 of the main body member 14, and effectively serves to retain the microcapsules 26, while simultaneously protecting the microcapsules 26 from premature rupture otherwise often associated with handling or other mechanical shock. By retaining the microcapsules 26 within a predefined boundary, the adhesive 24 adjacent of the periphery of the main body portion 14 is not subject to degradation.

Further in the preferred embodiment, the composite dispensing material 28 is covered by a removable protective layer 30 which extends over the entire upper surface 22 of the main body member 14. The protective layer 30 may be formed of silicone-coated paper or any other suitable material which may be readily stripped away from the adhesive coated upper surface 22 when the use of the apparatus 10 is required. The protective layer 30 permits the apparatus 10 of the present invention to be easily stacked prior to use and may also serve to at least partially activate the microencapsulated disinfectant material by rupturing some of the capsules 26 upon removal.

The apparatus 10 of the first preferred embodiment of the present invention further includes a flexible sheet material 32 permanently attached to a second or lower side 34 of the main body member 14. The flexible material 32 is preferably constructed of a thin polyethylene sheet or like material which is substantially resistant to penetration by sharp instruments and impervious to fluid. It should be appreciated by those skilled in the art that the adhesive 24 and the composite dispensing material 28 can alternatively be applied directly to the sheet material 32.

Turning to FIG. 6, an apparatus 10' constructed in accordance with a second preferred embodiment of the present invention is illustrated. For ease of reference, similar elements between the first embodiment and second embodiment are identified with like reference numerals identified with a prime. The main body portion 14' of the second preferred embodiment of the present invention includes a narrow strip of pressure-sensitive adhesive 24' provided adjacent the perimeter of the upper surface 22' of the main body portion 14'. The apparatus 10' of the second preferred embodiment further includes a first predetermined fold line 20a and a second predetermined fold line 20b, the significance of which will become more readily apparent below during the discussion of the operation of the present invention.

The first and second predetermined fold lines 20a,20b are interdisposed by an intermediate area 36. In the exemplary embodiment illustrated, the first and second predetermined fold lines 20a,20b intersect the longitudinal midline of the main body portion 14' at a first longitudinal edge 38 thereof. Preferably, the first and second predetermined fold lines 20a,20b diverge on opposite sides of the midline of the main body portion 14'.

The method of producing composite dispensing material 28 heretofore described will now be detailed. This method generally includes the steps of preparing an aqueous phase in the form of a pourable or flowable slurry mixture by mixing an aqueous liquid carrier such as water and micropackaged active ingredient particles in the range of 1%–60% by weight of the aqueous phase. Microencapsulated products are conveniently supplied dispersed in de-ionized water. The water carrier protects the beads or microcapsules during transport and handling. A surfactant wetting agent is also mixed in the aqueous phase for adjusting the surface tension of the aqueous phase to produce open cell foam upon polymerization with the prepolymer phase. An oil soluablizer may also be included in the aqueous phase for imparting lipophilic characteristics. Lipophilic characteristics for the resulting composite dispensing material are advantageous where the active ingredient or functional liquid is an oil and the substrate foam is able to absorb the oil upon release from the particles.

The method further includes mixing the aqueous phase with a prepolymer phase in ratio by weight of aqueous phase to prepolymer phase in the range of at least approximately 0.02/1 or greater and preferably 1/1 or greater and foam polymerizing the aqueous phase and prepolymer phase resulting in the open foam substrate and micropackage particle composite with the particles distributed over and bonded to the surfaces of the open foam substrate. Sufficient excess water is included in the aqueous phase for cooling the foam polymerization reaction of the aqueous phase and prepolymer phase and for limiting the reaction temperature so that it does not exceed 130° F. (54° C.).

A significant advantage of the described method of producing the composite dispensing material of the present invention is that the mixing of the aqueous dispersion of microcapsule beads or polymer lattices with the hydrophilic urethane prepolymer, does not destroy the integrity of the micropackages or microcontainment systems. Conventionally, urethane foam polymerization creates exothermic temperatures in excess of the rupture temperature of the microcapsules or polymer lattices. Foam system exothermic reactions can generate temperature which destroy the containment walls or volatilize the active ingredient of the microcapsules or micropackages. A temperature range between 180°–210° F. (82°–99° C.) is generally the heat rupture limit for such microcontainment systems. According to the present invention, the exothermic heat is controlled and the temperature of the reaction limited so that at most, it does not exceed 120° F. (49° C.) and normally it does not even exceed a temperature range of 100°–110° F. (38°–43° C.) for a reaction starting at room temperature.

In the preferred foams of the method, the aqueous phase and prepolymer phase are mixed together in ratio by weight of aqueous phase to prepolymer phase in the range of at least approximately 0.02/1 or greater, but preferably in the range of 1/1 to 12/1 and within that range, the preferred range of 1/1 to 8/1. At a ratio of 12/1 for aqueous phase to prepolymer phase, the resulting composite dispensing material is less cohesive, but usable, and abrades away like an eraser. At a ratio of 8/1, the composite dispensing material 28 achieves desired characteristics of adhesive structure. At the intermediate ratio, for example of 4/1, the resulting composite dispensing material 28 gives desired softness suitable for applications to the skin, including but not limited to cosmetics applications. At the lower ratio of 1/1, a tougher foam substrate is produced for heavier duty applications.

It will be appreciated by those skilled in the art, that it may be necessary to remove excess moisture from the foam. The excess moisture can be evaporated using, for example, oven drying of the foam to remove residual water. Advantageously, the composite material structure affords protection to the microcapsules 26 during heat drying. The foam substrate also protects the microcapsules 26 from premature rupture and release of active ingredients during handling and mechanical impacts. However, a firm squeeze compressing the foam, or the calculated application of other stress designed to break the containment walls, functions to sufficiently release the active ingredient from the capsules 26. The microcapsules 26 or other micropackages can be successfully completed with the foam substrate according to this method in sizes ranging at least from 5 microns to 5,000 microns (0.0002 to 0.2 inches).

In the construction of the exemplary embodiments illustrated throughout the Figures, the microcapsulated active ingredient particles or capsules 26 are distributed and applied over the surface of release paper 30. The aqueous phase is prepared without incorporation of the microcapsulated particles. After mixing the aqueous phase and prepolymer phase, the mixture is spread over and on the release paper 30 and layer of microcapsules 26 across the surface of the release paper 30. The resultantly formed sheet of composite dispensing material 28 is subsequently bonded to the surface of the main body member 14.

Figure 4:
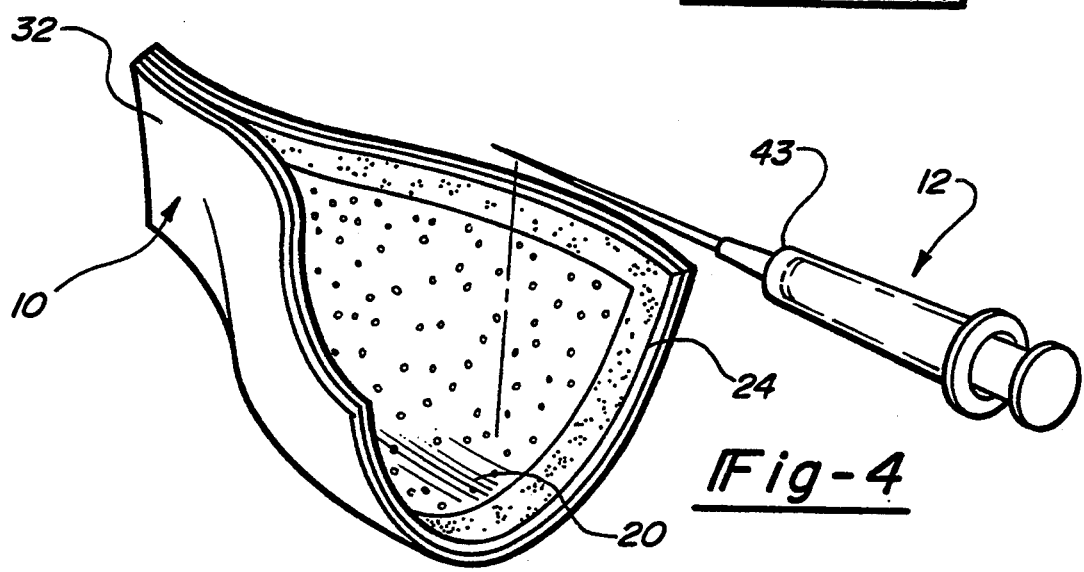
FIG. 4 is a perspective view of the apparatus of FIG. 1 shown with a first end thereof joined and a sharp instrument in place prior to envelopment.

Referring specifically to FIG. 4, the use of the apparatus 10 of the present invention heretofore detailed will be described. Significantly, operation of the present invention can be carried out by a single individual with only one hand. Advantageously, handling of potentially infectious sharp instruments can be quickly and easily brought within control through a minimized amount of contact. Prior to the use of the sharp instrument, whether it be a disposable needle, suture, scalpel or the like, the apparatus 10 of the present invention can be prepped for use such that the potentially contaminated sharp instruments can be enveloped and decontaminated through minimal effort and minimal risk. In this regard, the method of the present invention for enveloping and decontaminating a sharp instrument prior to disposal includes the removal of the protective layer from the upper surface 22 of the main body portion 14. The act of removing the protective layer 30 exposes the pressure-sensitive adhesive layer 24 formed on the upper surface 22 and also serves to at least partially activate the microcapsulated disinfectant material by rupturing some of the capsules 26.

The method of the present invention next includes the step of folding over a first end 40 (See FIG. 3) of the first portion 16 until it comes in contact with the first end 42 (See FIG. 3) of the second portion 18, thereby urging the main body member 14 into a trough-like or cradle-like shape as illustrated in FIG. 4. The apparatus 10 of the present invention can then be placed on any planar surface near the site of the sharp instrument use. It will be appreciated by those skilled in the art, that it may be alternatively desirable, depending on the particular circumstances or hospital protocol involved, for the apparatus 10 to remain substantially planar (as shown in FIG. 1) until the sharp instrument is in place.

The cradle-like configuration of the main body portion 14 encourages the apparatus 10 of the present invention to remain in a state ready to accept the sharp instruments, namely with the longitudinal edges of the main body portion 14 curved upward (as shown in FIG. 4). This state is further facilitated through the construction of the second preferred embodiment of the present invention (FIG. 6) which incorporates the intermediate area 36 which is disposed between the first and second predetermined fold lines 20a,20b. This intermediate area 36 is adapted to provide a substantially planar surface on which the apparatus 10' of the second embodiment can more readily balance.

The stability of the apparatus 10' of the present invention can be further increased by providing a light-strength adhesive (not shown) on the exterior surface of the protective layer 32 adjacent the midpoint of a second end 44 of the main body portion. At this point, the apparatus is ready to receive one or more sharp instruments for envelopment and decontamination. If a disposable syringe 12 is involved, the syringe 12 can be positioned as is shown in FIG. 4 with the needle portion extending onto the upper surface 22 of the main body member 14. Preferably, the hub 43 of the syringe 12 is positioned adjacent the main body portion 14. With other sharp instruments such as sutures, scalpels and the like, the sharp instrument can be placed substantially in the middle of the main body portion. If desired, the sharp instrument can be forced through the composite dispensing material 28 into the closed foam of the main body portion 14, thereby facilitating retention of the sharp object to the upper surface 22 of the main body portion 14.

Figure 3:
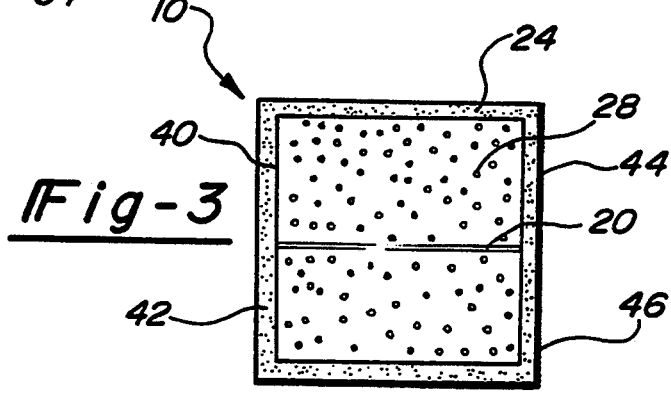
FIG. 3 is a top view of the apparatus of FIG. 1.

The method of the present invention next includes the step of folding over a second end 44 of the first portion 16 until it contacts a second end 46 of the second portion 18 (See FIG. 3). As such, the sharp instrument is completely enveloped within the main body portion 14. Closing of the main body portion 14 by urging the second end 44 of the first portion 16 into contact with the second end 46 of the second portion 18 is readily accomplishable by using one hand, thereby keeping the other hand out of potential risk or allowing the other hand to be otherwise used or both. After the sharp instrument is fully enveloped, slight pressure applied to the exterior of the protective layer 32 serves to insure complete adhesion of the pressure-sensitive adhesive 24 about the perimeter of the upper surface 22 of the main body portion 14, and also serves to insure complete activation of the microcapsulated disinfectant material through rupture of the capsules 26.

It will be appreciated by those skilled in the art, the teachings of the present invention extend significantly beyond the exemplary applications shown throughout the Figures. In this regard, incorporation of nonwoven fabric of other fabric skeleton or matrix in the composite dispensing material is useful in a variety of applications including scrubbing, abrasive and cosmetic products. The producing of such three-component dispensing materials and applicators can be accomplished by mixing the aqueous phase and prepolymer phase and dispensing the flowable mixture on a fabric material skeleton or matrix, impregnating the skeleton or matrix with the mixed aqueous phase and prepolymer phase, and passing the impregnated fabric skeleton or matrix through a pair of rollers, or other compressing elements for distributing the aqueous phase and prepolymer phase mixture through the skeleton or matrix and adjusting the density of the mixture. Upon foam polymerization the fabric skeleton or matrix is impregnated with the open foam substrate. The foam substrate fills the interstices of the fabric skeleton or matrix with defined density, bonding to the nonwoven fibers, while the micropackaged active ingredient particles are distributed over and bonded to the surfaces of the open foam substrate. Such a skeleton or matrix gives added strength to the dispensing material or applicating material for scrubbing, abrasive, or special purpose cosmetic applications.

Additionally, teachings of the present are applicable for improved dispensing of single component adhesives such as cyanoacrylic sugerglues. In many applications, surfaces to be bonded are not closely fitted for successful utilization of superglues. By utilizing the teachings of the present invention, a foam sheet composite dispensing material of bonded foam substrate and micropackaged adhesive microcapsules can be placed between the two surfaces filling surface irregularities between the surfaces to be glued, and dispensing the adhesive for example, in response to pressure between the two surfaces. An adhesive bond laminate results. Similarly, two component glue systems such as epoxy resin glue systems with separate micropackages or microcapsules of the epoxy glue and hardener can be distributed through the foam substrate of the composite dispensing material.

The foregoing discussion describes merely exemplary embodiments of the present invention. Those skilled in the art will readily recognize from the discussion included herein, and from the accompanying drawings and claims, that various changes, modifications and variations can be made therein without departing from the spirit and scope of the present invention as defined in the following claims.

What is claimed is:

1. An apparatus for enveloping and decontaminating a sharp instrument prior to disposal, the sharp instrument of the type used in contact with potentially infected bodily fluids, the apparatus consisting of:
   a substantially planar main body member having first and second sides, said first side including a first portion and a second portion, said main body member being sufficiently flexible to permit said first portion of main body member to be folded over on said second portion of said main body member;
   a flexible sheet material permanently attached to said second side, said flexible sheet material being resistant to penetration by said sharp instrument;
   means for substantially permanently affixing said first portion of said main body member to said second portion of said main body member; and
   means for decontaminating the sharp instrument;
   whereby said apparatus securely retains the sharp instrument for disposal.

2. The apparatus of claim 1, wherein said first portion is a mirror image of said second portion about a midline of said main body member, and further wherein said first portion and said second portion each include a first end and a second end.

3. The apparatus of claim 2, further comprising a predetermined fold-line coincident with said midline.

4. The apparatus of claim 3, wherein said means for substantially permanently affixing said first portion of said main body member to said second portion of said main body member comprises an adhesive disposed at least adjacent the periphery of said main body member.

5. The apparatus of claim 1, wherein said means for decontaminating comprises a micropackaged disinfectant.

6. The apparatus of claim 1, wherein said apparatus is adapted to envelop and decontaminate a plurality of sharp instruments.

7. The apparatus of claim 2, further comprising a first predetermined fold line and a second predetermined fold line, said first and second predetermined fold lines being disposed by an intermediate area.

8. The apparatus of claim 7, wherein said first and second fold lines diverge.

9. An apparatus for enveloping and decontaminating a sharp instrument prior to disposal, the sharp instrument of the type used in contact with potentially infected bodily fluids, said apparatus consisting of:
   a substantially planar main body member having first and second sides, said first side including a first portion and a second portion, said second portion being a substantial mirror image of said first portion about a midline disposed therebetween, said main body member being sufficiently flexible to permit said first portion of main body member to be folded over on said second portion of said main body member;
   a flexible sheet material permanently attached to said second side, said flexible sheet material being resistant to penetration by said sharp instrument;
   a first area of adhesive formed on said first portion;
   a second area of adhesive formed on said second portion;

a composite dispensing member disposed on said main body member, said composite dispensing member including a plurality of microcapsules, each of said microcapsules including an active disinfectant ingredient therein, said plurality of microcapsules being sufficiently frangible to rupture upon application of a predetermined stress;

whereby said apparatus securely retains and decontaminates the sharp instrument for disposal.

10. The apparatus of claim 9, wherein said first and second areas of adhesive each comprises a contact cement.

11. The apparatus of claim 10, wherein said composite dispensing material is disposed on both said first and second portions of said main body member, said composite dispensing material being sufficiently flexible to permit folding thereof.

12. The apparatus of claim 10, wherein said contact cement is disposed adjacent the periphery of said main body member.

13. The apparatus of claim 9, wherein said apparatus is adapted to envelop and decontaminate a plurality of sharp instruments.

14. The apparatus of claim 9, further comprising a first predetermined fold line and a second predetermined fold line, said first and second predetermined fold lines being interdisposed by an intermediate portion.

15. The apparatus of claim 14, wherein said first and second fold lines diverge.

16. A method of enveloping and decontaminating a sharp instrument prior to disposal, the sharp instrument of the type used in contact with potentially infected bodily fluids, the method consisting of the steps of:

providing an apparatus including a substantially planar main body member having first and second sides, said first side including a first portion and a second portion, both of said first and second sides including a first end and a second end, said main body member being sufficiently flexible to permit said first portion of main body member to be folded over on said second portion of said main body member, said apparatus further including a flexible sheet material permanently attached to said second side, said flexible sheet material being resistant to penetration by said sharp instrument;

applying an adhesive to said first portion and said second portion of said main body member for affixing said first portion to said second portion;

folding over said first end of said first portion until it contacts said first end of said second portion;

forming said main body portion into a partial trough-like shape for receiving the sharp instrument by applying pressure to said second side adjacent said first ends of said first and second portions to adhere said first portions together;

placing the sharp instrument on said first side of said main body portion;

folding over said second end of said first portion until it contacts said second end of said second portion;

applying a composite dispensing member on said first side of said main body portion, said composite dispensing member including a plurality of microcapsules, each of said microcapsules including an active disinfecting ingredient therein, said plurality of microcapsules being sufficiently frangible so as to rupture upon application of a predetermined stress; and applying a removable protective layer to said first side, thereby covering said composite dispensing material.

17. The method of claim 16, further comprising the steps of:

removing said removable protective layer, thereby at least partially activating said disinfectant.

18. The method of claim 17, further comprising the step of:

forming a predetermined fold line coincident with said midline.

19. The method of claim 17, further comprising the step of:

forming a first predetermined fold line and a second predetermined fold line, said first and second predetermined fold lines being interdisposed by an intermediate area.

* * * * *